（12） United States Patent
Gao

(10) Patent No.: US 10,181,251 B2
(45) Date of Patent: Jan. 15, 2019

(54) WEARABLE DEVICE, MONITORING METHOD AND INTELLIGENT MONITORING SYSTEM

(71) Applicant: BOE TECHNOLOGY GROUP CO., LTD., Beijing (CN)

(72) Inventor: Jian Gao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/327,896

(22) PCT Filed: Feb. 2, 2016

(86) PCT No.: PCT/CN2016/073133
§ 371 (c)(1),
(2) Date: Jan. 20, 2017

(87) PCT Pub. No.: WO2017/049830
PCT Pub. Date: Mar. 30, 2017

(65) Prior Publication Data
US 2018/0182229 A1    Jun. 28, 2018

(30) Foreign Application Priority Data
Sep. 21, 2015    (CN) .......................... 2015 1 0604219

(51) Int. Cl.
*G08B 21/24*    (2006.01)
*G06F 3/01*    (2006.01)
(Continued)

(52) U.S. Cl.
CPC ............... *G08B 21/24* (2013.01); *G06F 3/01* (2013.01); *A61B 5/681* (2013.01); *G06F 1/163* (2013.01)

(58) Field of Classification Search
None
See application file for complete search history.

(56) References Cited

U.S. PATENT DOCUMENTS

2015/0359992 A1* 12/2015 Sudo ...................... G16H 15/00
600/28
2016/0073951 A1* 3/2016 Kahn ................... G04G 13/026
600/595

FOREIGN PATENT DOCUMENTS

CN    203693601 U    7/2014
CN    104042193 A    9/2014
(Continued)

OTHER PUBLICATIONS

First Office Action for Chinese Application No. 201510604219.7, dated Aug. 1, 2017, 8 Pages.
(Continued)

*Primary Examiner* — Leon-Viet Nguyen
(74) *Attorney, Agent, or Firm* — Brooks Kushman P.C.

(57) ABSTRACT

A wearable device, a monitoring method and an intelligent monitoring system are disclosed. The wearable device includes an obtaining module, a timing module, a processing and a reminding module. The obtaining module is configured to obtain a current motion state of a user. The timing module is configured to generate a triggering signal when the time for which the user is in the current motion state reaches the predetermined time, so as to trigger the processing module to obtain a reminding signal corresponding to the current motion state of the user. The reminding module is configured to issue a reminder to remind the user to change the motion state.

14 Claims, 2 Drawing Sheets

(51) Int. Cl.
*A61B 5/00* (2006.01)
*G06F 1/16* (2006.01)

(56) References Cited

FOREIGN PATENT DOCUMENTS

| | | |
|---|---|---|
| CN | 104323763 A | 2/2015 |
| CN | 104754121 A | 7/2015 |
| CN | 104820499 A | 8/2015 |
| CN | 105224080 A | 1/2016 |
| WO | 2014190827 A1 | 12/2014 |

OTHER PUBLICATIONS

International Search Report and Written Opinion for Application No. PCT/CN2016/073133, dated Jun. 21, 2016, 10 Pages.
1st Chinese Office Action.
International Search Report and Written Opinion.

* cited by examiner

WEARABLE DEVICE, MONITORING METHOD AND INTELLIGENT MONITORING SYSTEM

CROSS-REFERENCE TO RELATED APPLICATIONS

This application is the U.S. national phase of PCT Application No. PCT/CN2016/073133 filed on Feb. 2, 2016, which claims priority to Chinese Patent Application No. 201510604219.7 filed on Sep. 21, 2015, the disclosures of which are incorporated in their entirety by reference herein.

TECHNICAL FIELD

The present disclosure relates to the field of intelligent device technology, and in particularly to a wearable device, a monitoring method and an intelligent monitoring system.

BACKGROUND

Smart watches usually have built-in intelligent operating systems and can connect with the Internet or mobile phones, thereby going beyond the only function of timing in the past. However, the smart watches in the related art can only accomplish commonly used functions such as recording information, displaying information of incoming calls, providing weather forecast information and performing voice communications. In the context of the Internet of Things, there lacks a technical portal for providing functional technologies that achieve interconnection between people and between people and things, and better user experiences.

SUMMARY

The present disclosure provides a wearable device and a monitoring method, so as to implement monitoring of a user state through the wearable device and achieve interconnection between people and things.

The present disclosure further provides an intelligent monitoring system which includes a wearable device, so as to remotely monitor a user's state through the wearable device and achieve interconnection between people.

In order to solve the above-mentioned problem, the embodiments of the present disclosure provide a wearable device. The wearable device includes: a motion state obtaining module configured to obtain a current motion state of a user; a timing module configured to set a predetermined time, calculate a time for which the user is in the current motion state, and generate a triggering signal when the time for which the user is in the current motion state reaches the predetermined time; a processing module connected with the motion state obtaining module and the timing module and configured to obtain a first reminding signal corresponding to the current motion state of the user when triggered by the triggering signal; and a reminding module configured to issue a first reminder, based on the first reminding signal, to remind the user to change the motion state.

The embodiments of the present disclosure further provide an intelligent monitoring system, which includes a remote terminal and the above-mentioned wearable device. The remote terminal is configured to receive a body parameter of the user obtained by the wearable device.

The embodiments of the present disclosure further provide a monitoring method using the above-mentioned wearable device. The method includes: obtaining a current motion state of a user; setting a predetermined time, calculating a time for which the user is in the current motion state, and generating a triggering signal when the time for which the user is in the current motion state reaches the predetermined time; obtaining a first reminding signal corresponding to the current motion state of the user when triggered by the triggering signal; and issuing, based on the first reminding signal, a first reminder to remind the user to change the motion state.

The above-mentioned solutions of the present disclosure have the following beneficial effects: the wearable device is provided with the obtaining module for obtaining the current motion state of the user; the triggering signal is generated when the time for which the user is in the current motion state reaches the predetermined time, so as to trigger the obtaining of the reminding signal corresponding to the current motion state of the user; and the reminder is issued to remind the user to change the motion state which lasts for a long time, so that the purpose of protecting the user's health and the interconnection between people and things are achieved.

BRIEF DESCRIPTION OF THE DRAWING

In order to more clearly illustrate the embodiments of the present disclosure or the technical solutions in the related art, drawings which are required to be used in the description of the embodiments or related art will be briefly described below. Apparently, the drawings in the following description relate to only some embodiments of the present disclosure. It will be apparent to those skilled in the art that other drawings may be derived from the drawings without any creative work.

DETAILED DESCRIPTION

The present disclosure will be specifically described in conjunction with accompanying drawings and embodiments. The following embodiments are merely illustrative of the present disclosure and are not intended to limit the scope of the present disclosure.

Figure 1:
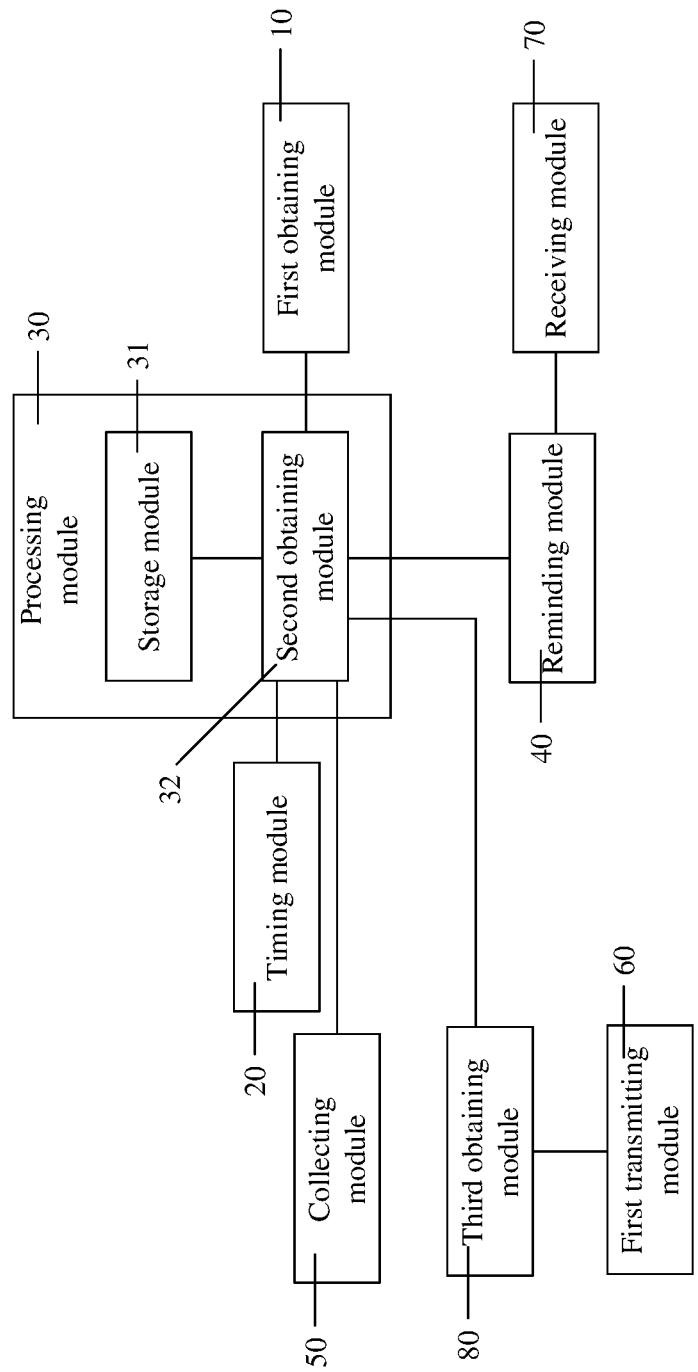
FIG. 1 illustrates a block diagram of a wearable device according to an embodiment of the present disclosure.

As shown in FIG. 1, an embodiment of the present disclosure provides a wearable device. The wearable device includes a first obtaining module 10, a timing module 20 and a processing module 30. The first obtaining module (herein also referred to as a motion state obtaining module) 10 is configured to obtain a current motion state of a user. The timing module 20 is configured to set a predetermined time, calculate a time for which the user is in the current motion state, and generate a triggering signal when the time for which the user is in the current motion state reaches the predetermined time. The processing module 30 is connected with the first obtaining module 10 and the timing module 20 and is configured to obtain a first reminding signal corresponding to the current motion state of the user when triggered by the triggering signal.

The wearable device further includes a reminding module 40 configured to issue a first reminder, based on the first reminding signal, to remind the user to change the motion state.

The wearable device of the present disclosure is capable of monitoring the current motion state of the user, and reminding the user to change the motion state which has last for a long time, thereby protecting the user's health and achieving the interconnection between people and things.

In some embodiments, the wearable device is a smart device installed with an operating system, e.g. a smart watch, a smart bracelet, a smart necklace and other wearable devices. The reminding module 40 may issue the first reminder by a sound, displaying captions or LED light flashing.

Specifically, the processing module 30 includes a storage module 31 and a second obtaining module 32. The storage module 31 stores a correspondence between the motion state of the user and the first reminding signal in advance. The second obtaining module 32 (herein also referred to as a reminding signal obtaining module) obtains, from the storage module 31, the first reminding signal corresponding to the current motion state of the user when triggered by the triggering signal which is generated by the timing module 20.

Apparently, the motion state of the user includes a quiescent state and a moving state. It is not appropriate to issue, in all scenarios, a reminder by merely monitoring the current motion state of the user. This approach has some limitations. For example, when the user is in an office and in the quiescent state for a long time, it indicates that the user maintains a fixed sitting gesture for a long time, and thus the user needs to be reminded to change the long-time fixed sitting gesture to protect the user's health. However, when the user is at home and in the quiescent state for a long time, which may indicate the user is sleeping, the reminder for reminding the user to change the gesture may affect the user's sleep quality and affect the user's health.

Therefore, in practical implementations, a collecting module 50 is provided for collecting a parameter of an environment in which the user is currently located. The processing module 30 is configured to obtain the first reminding signal corresponding to the parameter of the environment in which the user is currently located and the motion state. In the scenario that the processing module 30 includes the storage module 31, the correspondence between the first reminding signal and the parameter of the environment and the motion state is stored in the storage module 31, the second obtaining module 32 obtains, from the storage module 31, the first reminding signal corresponding to the parameter of the environment in which the user is currently located and the motion state. In this way, the reminder is issued in consideration of the parameter of the environment in which the user is currently located and the motion state, so as to remind the user to change the motion state.

The parameter of the environment may include a volume, a light intensity and a position of the user. The collecting module 50 includes a series of sensors for obtaining the parameter of the environment. In order to accurately collect the parameter of the environment, the collecting module 50 is arranged at the surface of the wearable device. In the example of the smart watch, the collecting module 50 may be arranged at the surface of the dial.

For the purpose of reminding, in consideration of the parameter of the environment in which the user is currently located and the motion state, the user to protect the user's health, the parameter of the environment in which the user is currently located may be set for a particular scenario. In a particular scenario, the first reminding signal is set for the case that the user is in a motion state for a long time. For example, in a scenario where the user is currently in an office (position parameter), the environmental volume is below a set value and the user is in the quiescent state, the first reminder is used to remind the user to change the fixed sitting gesture. In a scenario where the user is at home (position parameter), the light intensity is below a set value and the user is in the quiescent state, the first reminder is not issued to remind the user to change the fixed sitting gesture. In the scenario where the user is currently outdoors (position parameter) and the user is in the moving state, the first reminder is used to remind the user to rest to protect the user's health from over frequent exercises.

The scenario may also include a meeting scenario, a hill climbing scenario and a night downtown scenario.

In the embodiment of the present disclosure, the wearable device may further include a third obtaining module 80 (herein also referred to as a body parameter obtaining module) configured to obtain the body parameter of the user and monitor the user's health status based on the body parameter. The body parameter may include, but is not limited to, a temperature parameter, a heartbeat number, a pulse parameter, etc. Specifically, the values of the body parameters may be obtained by corresponding sensors.

Further, the wearable device may include a first transmitting module 60 (herein also referred to as a body parameter transmitting module) configured to transmit the body parameter to a remote terminal so that the remote terminal monitors the user's health status. In some embodiments, the first transmitting module 60 may be a wifi transmitting module which wirelessly transmits the current motion state of the user and the time for which the user has been in the current motion state in real time so that the remote terminal monitors the user's health status. In a specific implementation, parents may remotely monitor the health status of the kid wearing the wearable device according to the embodiment of the present disclosure.

Apparently, the first transmitting module 60 may also be a USB transmitting module which stores the obtained body parameter of the user in the wearable device and regularly transmits the stored body parameter of the user to the remote terminal in a wired way.

When used for remotely monitoring, the wearable module may further include a receiving module 70 configured to receive a second reminding signal transmitted from the remote terminal. The reminding module 40 may issue a second reminder, based on the second reminding signal, to remind the user of some matters, e.g. going home for meals, getting up, taking medicine.

Optionally, the wearable module may include a third obtaining module 80, the first transmitting module 60 and the receiving module 70 at the same time, so as to transmit the body parameter of the user to the remote terminal, receive the reminding signal transmitted by the remote terminal and achieve the interaction with the remote terminal. Therefore, the wearable module has the abilities of achieving the interconnection between people and the interconnection between people and things, and thus has a wide range of applications. For example, the remote terminal may remind the user to take medicine, or have a rest, or go to hospital, etc., after learning the health status of the user wearing the wearable device. In an embodiment, the wearable device may further include a collecting module 50 configured to collect the parameter of the environment where the user is located, the parameter of the environment may be packaged with the body parameter of the user into data packets, and then the data packets are transmitted to the remote terminal, making the monitoring more comprehensive and reliable.

The wearable device according to the embodiment of the present disclosure specifically includes: the first obtaining module 10 configured to obtain the current motion state of the user; the collecting module 50 configured to obtain the parameter of the environment where the user is currently located which constitutes the current scenario; the timing module 20 configured to set the predetermined time, calculate the time for which the user is in the current motion state, and generate the triggering signal when the time for which the user is in the current motion state reaches the predetermined time; a storage module 31 configured to store in advance the correspondences between the motion state of the user and the first reminding signal in different scenarios; the second obtaining module 32 which is connected with the first obtaining module 10 and the timing module 20 and is configured to obtain from the storage module 31 the first reminding signal corresponding to the current motion state of the user in the current scenario when triggered by the triggering signal; the reminding module 40 configured to issue a first reminder, based on the first reminding signal, to remind the user to change the motion state; the third obtaining module 80 configured to obtain the body parameter of the user; the first obtaining module 60 configured to package the parameter of the environment and the body parameter of the user into data packets and transmit the data packets to the remote terminal in real time so that the remote terminal monitors in real time the health status of the user wearing the present wearable device; the receiving module 70 configured to receive the second reminding signal transmitted by the remote terminal, and the reminding module 40 is further configured to issue the second reminder based on the second reminding signal.

Figure 3:
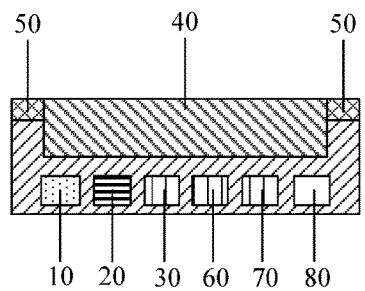
FIG. 3 illustrates a dial of a smart watch according to an embodiment of the present disclosure.

If the wearable device of the embodiment of the present disclosure is a smart watch, the first obtaining module 10, the timing module 20, the processing module 30, the reminding module 40, the collecting module 50, the first transmitting module 60, the receiving module 70 and the third receiving module 80 may be arranged at the dial of the smart watch, as shown in FIG. 3. Specifically, the reminding module 40 may be configured as a display screen at the outer surface of the dial. The collecting module 50 is arranged at the outer surface of the dial and at the periphery of the display screen. Other modules may be arranged at the inner surface of the dial. The inner surface is a surface contacting the wrist of the user when the user wears the smart watch, and the outer surface is a surface opposite to the inner surface.

For other wearable devices, the position of each module may be set based on the specific structures. Optionally, the collecting module 50 is arranged at the outer surface of the wearable device for ease of collecting the parameter of the environment. As such, if the reminding module 40 reminds the user by means of displaying captions, the reminding module 40 is arranged at the outer surface of the wearable device for ease of being viewed by the user.

An embodiment of the present disclosure further provides an intelligent monitoring system, which includes a remote terminal and the above-mentioned wearable device. If the wearable device includes the third obtaining module configured to obtain the body parameter of the user, the remote terminal is configured to receive the body parameter of the user obtained by the wearable device.

The body parameter of the user may be obtained accurately and in real time through the wearable device, and the user's health status is monitored. The wearable device has better timeliness and interaction experience when applied in remote monitoring. Especially, the wearable device has a wide application market regarding the child's custody.

Optionally, the remote terminal further includes a second transmitting module configured to transmit a second reminding signal to the wearable device. Specifically, the remote terminal may transmit a corresponding reminding signal based on the obtained body parameter of the user. Apparently, the remote terminal may transmit other types of reminding signals on its own, such as reminding the user to go home for meals, doing homework. The effective interaction between the remote terminal and the user wearing the wearable device may be achieved by arranging the second transmitting module.

Figure 2:
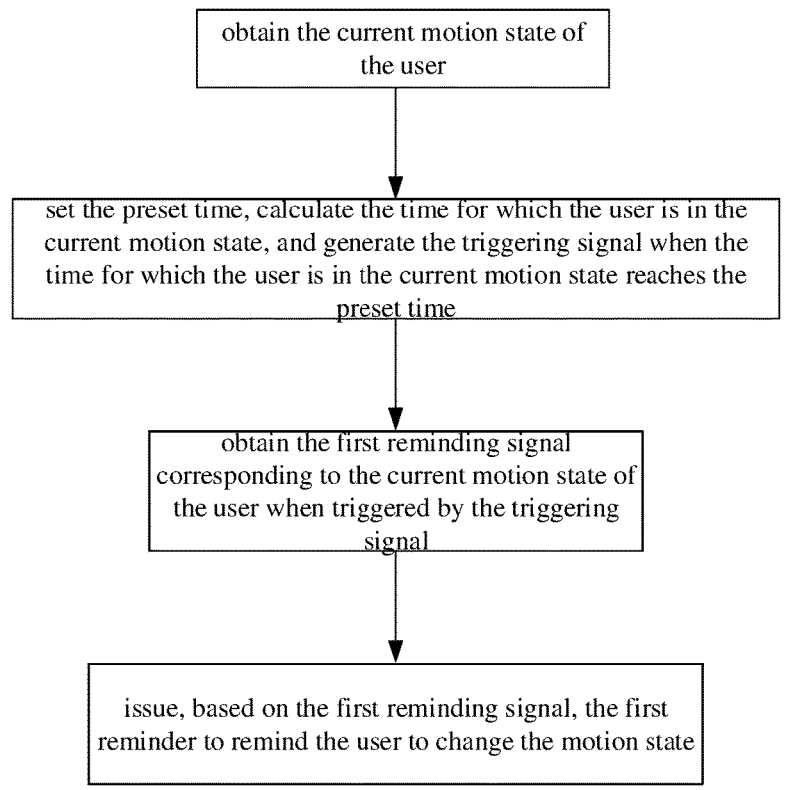
FIG. 2 illustrates a flow chart of a monitoring method using a wearable device according to an embodiment of the present disclosure.

As shown in FIG. 2, based on the same inventive concept, an embodiment of the present disclosure further provides a monitoring method using the above-mentioned wearable device. The monitoring method includes: obtaining a current motion state of a user; setting a predetermined time, calculating a time for which the user is in the current motion state, and generating a triggering signal when the time for which the user is in the current motion state reaches the predetermined time; obtaining the first reminding signal corresponding to the current motion state of the user when triggered by the triggering signal; and issuing, based on the first reminding signal, a first reminder to remind the user to change the motion state.

The above-mentioned monitoring method obtains the current motion state of the user and the time for which the user is in the current motion state to remind the user to change the current motion state and remind the user to change the motion state which lasts for a long time, thereby achieving the purpose of protecting the user's health.

In a particular embodiment, the step of obtaining the first reminding signal corresponding to the current motion state of the user specifically includes: storing a correspondence between the motion state of the user and the first reminding signal; and obtaining, according to the stored correspondence, the first reminding signal corresponding to the current motion state of the user when triggered by the triggering signal.

In practical implementations, it is necessary to set the first reminding signal corresponding to the current motion state based on the scenario where the user is located. The scenario is represented by the parameter of the environment where the user is currently located. Then, the above-mentioned monitoring method further includes: collecting the parameter of the environment in which the user is currently located; and obtaining the first reminding signal corresponding to the parameter of the environment in which the user is currently located and the motion state. Specifically, the correspondences between the motion state of the user and the first reminding signal in different scenarios may be stored in advance, and the first reminding signal corresponding to the current motion state of the user is obtained for the current scenario according to the correspondences.

In an embodiment of the present disclosure, the above-mentioned monitoring method further includes: obtaining a body parameter of the user; and transmitting the body parameter of the user to a remote terminal, so as to achieve the monitoring of the user's health status by the remote terminal.

Further, the parameter of the environment in which the user is currently located and the body parameter of the user are packaged into data packets and the data packets are transmitted to the remote terminal, making the monitoring more comprehensive and reliable.

When used for remotely monitoring, the above-mentioned monitoring method may further include: receiving a second reminding signal transmitted from the remote terminal; and issuing a second reminder based on the second reminding signal.

Optionally, the above-mentioned monitoring method includes: obtaining a body parameter of the user; transmitting the body parameter of the user to a remote terminal; receiving a second reminding signal transmitted from the remote terminal; and issuing a second reminder based on the second reminding signal.

By way of the above-mentioned steps, it is possible to transmit the body parameter of the user to the remote terminal and receive the reminding signal transmitted by the remote terminal, thereby achieving the interaction with the remote terminal and extending the application range.

The monitoring method provided by the present disclosure monitors the motion state of the user through the wearable device and reminds the user to change the motion state which lasts for a long time, thereby achieving the purpose of protecting the user's health and extending the human-computer interaction function of the smart wearable device.

The above-mentioned embodiments are merely optional embodiments of the present disclosure. It should be noted that improvements and substitutions may be made by those skilled in the art without departing from the technical principles of the present disclosure. These improvements and substitutions should also be considered within the scope of protection of the present disclosure.

What is claimed is:

1. A wearable device, comprising:
   a motion state obtaining module configured to obtain a current motion state of a user;
   a timing module configured to set a predetermined time, calculate a time for which the user is in the current motion state, and generate a triggering signal when the time for which the user is in the current motion state reaches the predetermined time;
   a processing module connected with the motion state obtaining module and the timing module and configured to obtain a first reminding signal corresponding to the current motion state of the user when triggered by the triggering signal;
   a reminding module configured to issue a first reminder, based on the first reminding signal, to remind the user to change the motion state; and
   a collecting module configured to collect a parameter of an environment in which the user is currently located, wherein the parameter of the environment comprises a volume, a light intensity, and a position of the user, wherein the collecting module is arranged at a surface of the wearable device and includes a series of sensors for obtaining the parameter of the environment,
   wherein the processing module is further configured to obtain the first reminding signal corresponding to the parameter of the environment in which the user is currently located and the motion state of the user.

2. The wearable device according to claim 1, further comprising:
   a body parameter obtaining module configured to obtain a body parameter of the user.

3. The wearable device according to claim 2, further comprising:
   a body parameter transmitting module configured to transmit the body parameter of the user to a remote terminal.

4. The wearable device according to claim 3, further comprising: a receiving module configured to receive a second reminding signal transmitted from the remote terminal, wherein
   the reminding module is further configured to issue a second reminder based on the second reminding signal.

5. The wearable device according to claim 1, wherein the first reminding signal is used to remind the user to adjust a fixed sitting gesture in the case that the user is in an office, an environmental volume is lower than a predetermined value, and the user is in a quiescent state.

6. The wearable device according to claim 1, wherein the processing module comprises:
   a storage module configured to store the first reminding signal corresponding to the motion state of the user; and
   a reminding signal obtaining module configured to obtain, from the storage module, the first reminding signal corresponding to the current motion state of the user when triggered by the triggering signal.

7. The wearable device according to claim 1, wherein the wearable device is a watch, a necklace or a bracelet.

8. An intelligent monitoring system, comprising:
   a remote terminal; and
   a wearable device, the wearable device including
      a motion state obtaining module configured to obtain a current motion state of a user;
      a timing module configured to set a predetermined time, calculate a time for which the user is in the current motion state, and generate a triggering signal when the time for which the user is in the current motion state reaches the predetermined time;
      a processing module connected with the motion state obtaining module and the timing module and configured to obtain a first reminding signal corresponding to the current motion state of the user when triggered by the triggering signal;
      a reminding module configured to issue a first reminder, based on the first reminding signal, to remind the user to change the motion state; and
      a collecting module configured to collect a parameter of an environment in which the user is currently located, wherein the parameter of the environment comprises a volume, a light intensity, and a position of the user, wherein the collecting module is arranged at a surface of the wearable device and includes a series of sensors for obtaining the parameter of the environment,
      wherein the processing module is further configured to obtain the first reminding signal corresponding to the parameter of the environment in which the user is currently located and the motion state of the user; and
   wherein the remote terminal is configured to receive a body parameter of the user obtained by the wearable device.

9. The intelligent monitoring system according to claim 8, wherein the remote terminal further comprises a reminding signal transmitting module for transmitting a second reminding signal to the wearable device.

10. A monitoring method using a wearable device including a motion state obtaining module, a timing module, a processing module connected with the motion state obtaining module and the timing module, a reminding module, and a collecting module, the method comprising:
    obtaining a current motion state of a user using the motion state obtaining module;

setting a predetermined time, calculating a time for which the user is in the current motion state, and generating a triggering signal when the time for which the user is in the current motion state reaches the predetermined time using the timing module;

obtaining, using the processing module, a first reminding signal corresponding to the current motion state of the user when triggered by the triggering signal;

issuing, using the reminding module, based on the first reminding signal, a first reminder to remind the user to change the motion state;

collecting a parameter of an environment in which the user is currently located using the collecting module, wherein the parameter of the environment comprises a volume, a light intensity, and a position of the user, wherein the collecting module is arranged at a surface of the wearable device and includes a series of sensors for obtaining the parameter of the environment; and obtaining, using the processing module, the first reminding signal corresponding to the parameter of the environment in which the user is currently located and the motion state of the user.

11. The method according to claim 10, further comprising:
obtaining a body parameter of the user.

12. The method according to claim 11, further comprising:
transmitting the body parameter of the user to a remote terminal.

13. The method according to claim 10, further comprising:
receiving a second reminding signal transmitted from the remote terminal; and
issuing a second reminder based on the second reminding signal.

14. The method according to claim 10, wherein the step of obtaining the first reminding signal corresponding to the current motion state of the user comprises:
storing a correspondence between the motion state of the user and the first reminding signal; and
obtaining, according to the stored correspondence, the first reminding signal corresponding to the current motion state of the user when triggered by the triggering signal.

* * * * *